United States Patent [19]

Ohno et al.

[11] Patent Number: 5,708,159

[45] Date of Patent: Jan. 13, 1998

[54] PROBE FOR DIAGNOSING INFECTIOUS DISEASES WHICH HYBRIDIZES WITH DNA FROM CANDIDA ALBICANS

[75] Inventors: Tsuneya Ohno, 15-16, Kita-Aoyama 3 chome, Minato-ku, Tokyo 107; Takuo Hirotsu; Hiroyuki Keshi, both of Tokyo; Akio Matsuhisa, Nara, all of Japan

[73] Assignees: Tsuneya Ohno, Tokyo; Fuso Pharmaceutical Industries, Ltd., Osaka, both of Japan

[21] Appl. No.: 416,831

[22] PCT Filed: Oct. 25, 1993

[86] PCT No.: PCT/JP93/01555

§ 371 Date: Jun. 19, 1995

§ 102(e) Date: Jun. 19, 1995

[87] PCT Pub. No.: WO94/10341

PCT Pub. Date: May 11, 1994

[30] Foreign Application Priority Data

Oct. 23, 1992 [JP] Japan .................................. 4-285802

[51] Int. Cl.$^6$ .............................. C07H 21/04; C12Q 1/68
[52] U.S. Cl. ............................. 536/24.32; 536/24.33; 536/23.1; 435/6; 935/8; 935/78
[58] Field of Search ........................... 536/24.32, 24.33, 536/23.1, 23.7; 435/6; 935/8, 78

[56] References Cited

U.S. PATENT DOCUMENTS

| | | | |
|---|---|---|---|
| 4,851,330 | 7/1989 | Kohne | 435/6 |
| 5,403,710 | 4/1995 | Weisburg et al. | 435/6 |
| 5,426,027 | 6/1995 | Lott et al. | 435/6 |

FOREIGN PATENT DOCUMENTS

| | | |
|---|---|---|
| 0 335 633 A2 | 10/1989 | European Pat. Off. . |
| 0 335 633 A3 | 10/1989 | European Pat. Off. . |
| 0 422 869 A2 | 4/1991 | European Pat. Off. . |
| 0 468 812 A2 | 1/1992 | European Pat. Off. . |

OTHER PUBLICATIONS

Barns et al., "Evolutionary Relationships among Pathogenic Candida Species and Relatives," *J. Bacteriology*, 173(7):2250–2255 (1991).

Cheung et al., "Development of DNA Probes for *Candida albicans*," *Diagn. Microbiol. Infect. Dis.*, 10:171–179 (1988).

Cutler et al., "*Candida albicans*– and *Candida stellatoidea*–Specific DNA Fragment," *J. Clinical Microbiology*, 26(9):1720–1724 (Sep., 1988).

Fox et al., "The Use of a DNA Probe for Epidemiological Studies of Candidiasis in Immunocompromised Hosts," *J. Infectious Diseases*, 159(3):488–494 (Mar., 1989).

Ganesan et al., "Molecular Cloning of the Secretory Acid Proteinase Gene from *Candida albicans* and Its Use as a Species–Specific Probe," *Infection & Immunity*, 59(9):2972–2977 (Sep., 1991).

Holmes et al., "Yeast–specific DNA Probes and Their Application for the Detection of *Candida albicans*," *J. Med. Microbiol.*, 37:346–351 (1992).

Miyakawa et al., "Isolation and Characterization of a Species–Specific DNA Fragment for Detection of *Candida albicans* by Polymerase Chain Reaction," *J. Clinical Microbiology*, 30(4)::894–900 (Apr., 1992).

(List continued on next page.)

*Primary Examiner*—Carla J. Myers
*Attorney, Agent, or Firm*—Marshall, O'Toole, Gerstein, Murray & Borun

[57] ABSTRACT

The invention provides a probe useful for rapidly detecting and identifying fungi causative of infectious diseases by digesting completely a DNA extracted from a fungus, e.g., *Candida albicans*, with EcoRI, inserting the same into an appropriate cloning vector, and selecting a probe containing DNA fragments unique to each fungus. The invention also provides a standard sequence suitable for making reference to a genomic DNA contained in a clinical specimen by elucidating the base sequence of the probe thus selected.

13 Claims, 5 Drawing Sheets

OTHER PUBLICATIONS

Oren et al., "Isolation and Characterization of a Species-Specific DNA Probe for *Candida albicans*," *Nucleic Acids Research*, 19(25):7113–7116 (1991).

Scherer et al., "A *Candida albicans* Dispersed, Repeated Gene Family and Its Epidemiologic Application," *Proc. Nat'l Acad. Sci., USA*, 85(5):1452–1456 (Mar., 1988).

Wilkinson et al., "A New, Sensitive Polynucleotide Probe for Distinguishing *Candida albicans* Strains and Its Use With a Computer Assisted Archiving and Pattern Comparison System," *J. Medical & Veterinary Mycology*, 30:123–131 (1992).

PROBE FOR DIAGNOSING INFECTIOUS DISEASES WHICH HYBRIDIZES WITH DNA FROM CANDIDA ALBICANS

FIELD OF THE ART

The present invention relates to a probe which is useful for detecting, identifying and diagnosing the causative fungi of infectious diseases.

BACKGROUND ART

In pathology, infection is defined as invasion and establishment of a foothold for growth in an organism by a pathogenic organism (hereinafter referred to as "bacterium"), then the outbreak of a disease caused by proliferation of the pathogenic organism in vivo depends upon the interrelationship between the resistance of the host and the virulence of bacteria.

In the infectious diseases, improvement in treatment methods of fungemia has been raised as an important issue, since the fungemia is a serious and urgent disease, in particular, if a patient is an infant suffering from cancer, the patient may die in a few days in its usual case, or die in one or two days in the terminal stage of the cancer with weakened resistance, therefore, the improvement in treatment methods thereof has been awaited.

In the infectious disease, phagocytes including neutrophils, monocytes and macrophages primarily work in defense of the body. In fungemia, appearance of fungi in the blood is thought as invasion of predominant fungi which have exuded from the texture of the phagocyte.

Bacteremia (including fungemia) is a state wherein the bacteria are exuded into the blood, and a large amount of antibiotic is administered to treat it wherein the causative bacteria are sensitive to the antibiotic. However, in general, since antibiotics lower the functions of the internal organ such as liver, it is necessary to pay an attention to reduce an administration of an ineffective antibiotic to a patient in a serious state.

When bacteremia is defined as a case wherein the ability of phagocytosis by cells cannot overcome the virulence of bacteria and then the bacteria spread through the blood in the whole body, generally, bacteremia with serious symptoms due to toxins produced by the bacteria is called as sepsis. Identification of sepsis, in the other word, establishment of its diagnosis requires checks on the following items: 1) clinical symptom, 2) culturing of specimen, 3) gram-staining of the bacteria contained in the specimen, and 4) shock state. Then, upon completing the checks on these items, the treatment method is determined. Accordingly, rapid and reliable identification of the bacteria has been awaited in the clinical site.

In the methods for detecting and identifying bacteria in a bacteremia-specimen, it is a common procedure to identify a specimen which has positive signal in a selective medium using a routine process by way of a culture bottle. However, it is actually quite difficult to successfully culture the bacteria from this blood specimen, moreover, if a large dose of antibiotic is administered when bacteremia was suspected, bacteria in the blood will not be cultured and grown in many cases in spite of the fact that bacteria are contained in the blood specimen, therefore, the rate of positive case by way of a culture bottle becomes extremely low.

Although available subroutine methods include instrumental analysis method of constituents of bacteria and metabolic products by bacteria (See Yoshimi Benno, "Quick identification of bacteria with gas chromatography", Rinsho Kensa, Vol. 29, No. 12, November 1985, Igaku Shoin.), a method utilizing a specific antibody (See Japanese Patent Provisional Publication No. 60-224068.), and a hybridization method utilizing a specificity of DNA (Japanese Phase Patent Provisional Publication No. 61-502376) have been developed, any of which is required separation of the bacteria, and culturing and growing of the bacteria.

On the other hand, as an established method based on the function of the phagocyte in infectious diseases, there is a method to examine a stained smear of buffy coat wherein leukocytes in the blood sample are concentrated, under an optical microscope. Generally speaking, the rate of detection of bacteria in buffy coat specimens from adult bacteremia patients is 30% at most, which is similar to that in blood specimens from an earlobe, however, it was reported that in case that the patients were newborn children, bacteria had been detected in seven cases in ten cases (70%), therefore, information concerning the presence of bacteria in peripheral blood obtained by a microscopic examination on a smear is an important index for treatment.

Since the above mentioned conventional methods necessitate the pretreatment which requires at least three to four days in total containing one to two days for selective isolation of bacteria from a specimen, one day for cultivation, and one or more days for operation of fixation, and the culture thereof is continued in practice until the bacteria grow, the pretreatment would require one week or more even for many of C.B. (culture bottle)-positive cases, therefore, this has been a factor in high mortality of C.B.-positive patients being examined by the conventional methods. For example, according to a report published in "The Journal of the Japanese Association for Infectious Diseases", Vol. 58, No. 2, p. 122, 1984, even though the positive rate of the blood culture was 28.6% (163 cases/569 cases), the mortality was as high as 84.6% (138 cases/163 cases).

Further, it may be impossible to distinguish contamination by indigenous bacteria at the cultivation thereof. For example, *Staphylococcus epidermides*, which is one of the causative bacteria of bacteremia, stayed also on the skin of the normal person, then, there has been a risk on contamination of a specimen with this bacterium when a needle is inserted into the skin.

As an important matter, under such circumstances above, since many bacteria in a specimen to be cultured have been incorporated into phagocyte and are dead or stationary immobilized due to antibiotics administered, the number of bacteria that can be grown is small even under appropriate conditions for cultivation, thereby, the actual detection rate of bacteria is as low as about 10% when clinical culture specimen is employed. In the other words, for the present, 90% of the examined blood, which has been cultured for further one or more days, of the patient suspected clinically as suffering from bacteremia could not be clarified for the presence of bacteria after all.

Thus, many cases of bacteremia are unclear as to whether the infectious disease results from bacteria or fungi, and the method for treatment employed such as antibiotics is greatly different according to the kind of causative bacteria. In light of the situation above, the present practice depends on a treatment to be started when bacteremia is clinically suspected without awaiting the detection results, that is to say, a trial and error method wherein an antibiotic having the effectiveness for the widest range of the causative bacteria is administered first, and if the antibiotic is not effective after one or two days, another antibiotic will be tested.

According to the method to stain the bacteria in the specimen, the constituents of the living body are likewise stained together with bacteria, therefore, an experience to identify bacteria quickly according to their image through a microscope is required, then there may be cases that can be hardly identified.

Although bacteremia is a disease wherein a rapid and exact diagnosis has been required as stated above, the conventional diagnosis method could not have responded to such requirements.

Disclosure of the Invention

The present invention was established in view of the above-described problems in the art, and is directed to a probe having a specific reactivity with DNA or RNA obtained from wide range of causative fungi of the infectious diseases including fungus *Candida albicans*, further, provides the clarified base sequence of DNA in the probe.

Moreover, when a primer is designed with reference to information on said base sequence of the probe, causative fungi can be identified without the hybridization, by amplifying DNA with PCR technique.

Additionally, non-radioactive probe, for example, a biotinylated probe is used for hybridization, detection even in a conventional laboratory can be performed without a radio isotope handling facility, and detection process will be carried out rapidly and simply.

BEST MODE FOR CARRYING OUT THE INVENTION

Followings are examples of the probes from *Candida albicans*:

EXAMPLE 1

DNA Probe from *Candida albicans*

(1) Selection of DNA Probe from *Candida albicans*

Clinical isolate of *Candida albicans* (C.A.-26) was cultivated overnight in Sabouraud's medium, collected the cultivated fungi, added thereto Zymolyeis (Seikagaku Kogyo) instead of lysozyme, then, genomic DNA was extracted according to Saito-Miura's Method ("Preparation of Transforming Deoxyribonucleic Acid by Phenol Treatment", Biochem. Biophys. Acta, Vol.72, pp.619–629 (1963)).

The extracted DNA was digested completely with restriction enzyme EcoRI and was random cloned into vector pGEM-3Z. DNA fragment specific for *Candida albicans* was selected from the clones so obtained.

Figure 1:
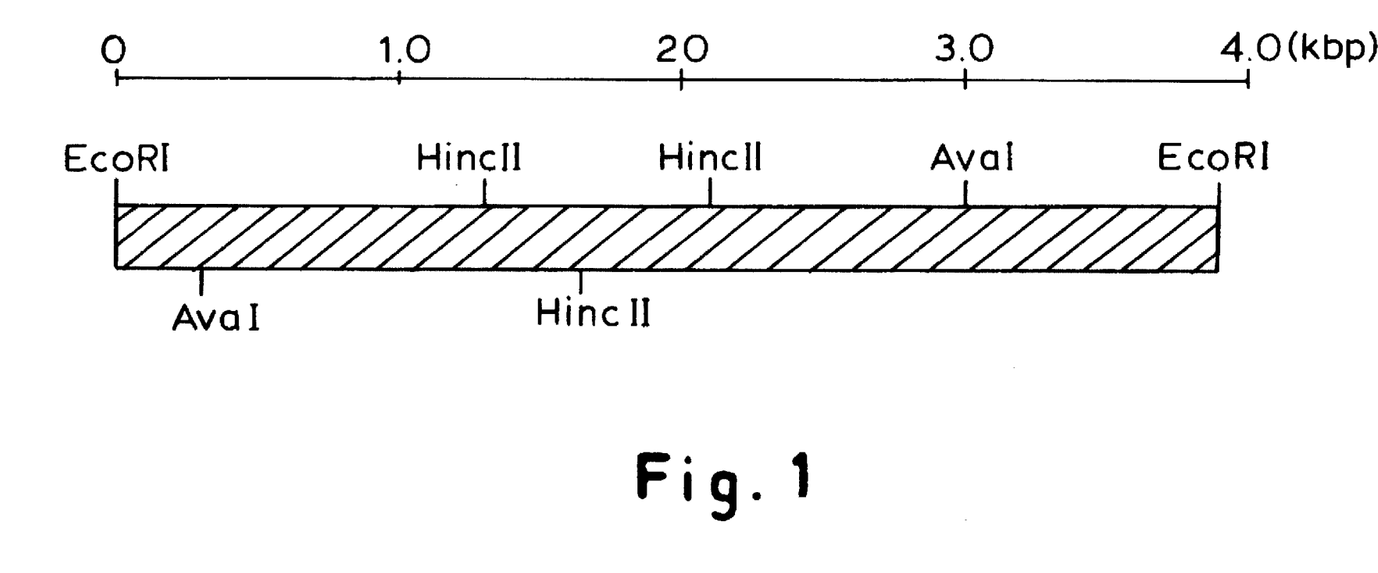
FIG. 1 is a restriction enzyme map of EcoRI fragment on a probe for detecting *Candida albicans*.

The selected DNA fragment was then designated as probe CA-26 and restriction map thereof was illustrated in FIG. 1.
(2) Evaluation on Species-Specificity of DNA Probe from *Candida albicans*

Reactivities between the DNA fragment selected in the above Example 1 (1) and DNA from several kinds of causative bacteria of infectious diseases were examined according to the following method.

First, as subject strains for an examination, clinical isolates (total 31 strains) were prepared.

Then, DNA of each clinical isolate was extracted according to the method of Example 1 (1), and samples for dot-blot-hybridization were obtained by spotting certain amount (e.g., 5 µg/µl) of the extracted DNA to a Byodyne nylon filter (type B), air-drying, denaturing with 0.5N NaOH-1.5M NaCl for 10 minutes, neutralizing with 0.5M Tris-Cl (pH 7.5)-1.5M NaCl for 10 minutes, washing with 1% SSC for 5 minutes, and air-drying. Hybridization on DNA probes prepared from *Candida albicans* and labelled with digoxigenin-dUTP by way of DNA labeling and detection kit (Cat No. 1175033: Boehringer Mannheim Biochemica), was then performed overnight according to Manual of Maniatis (Maniatis, et al., "Molecular Cloning (A Laboratory Manual)", Cold Spring Harbour Laboratory (1982)), under the condition of 45% formamide, 5×SSC, 42° C., following prehybridization under the same condition for 2 hours at 42° C.

Samples obtained through overnight hybridization were washed twice with 1×SSC, 0.1% SDS for 20 minutes at 50° C., then, were incubated for 30 minutes with 2% blocking reagent (Skimmed milk: Yukijirushi). Thus obtained filters were incubated with about 5 ml of diluted antibody-conjugate solution (150 mU/ml (1:5000)) for 30 minutes, washed twice with 50 ml of buffer (0.1M Tris-Cl (pH 7.5), 0.15M NaCl) for 15 minutes to remove nonbound antibody-conjugate, equilibrated with 10 ml of A.P. 9.5 for 2 minutes. The filters were sealed in a plastic bag containing 10 ml of NBT/BCIP (BRL) and incubated to detect by color reaction, and the reaction was terminated by washing the membranes with 30 ml of TE buffer for 10 minutes.

Experimental results on reactivity on hybridization between a probe of the present invention and DNA from each clinical isolate are illustrated in the following Table 1.

TABLE 1

| Strain Name | Reactivity |
|---|---|
| bacteria | |
| *Staphylococcus aureus* | − |
| *Staphylococcus epidermidis* | − |
| *Enterococcus faecalis* | − |
| *Escherichia coli* | − |
| *Klebsiella pneumoniae* | − |
| *Streptococcus pneumoniae* | − |
| *Streptococcus sanguis* | − |
| *Pseudomonas fluorescens* | − |
| *Pseudomonas maltophilia* | − |
| *Pseudomonas diminuta* | − |
| *Pseudomonas putida* | − |
| *Pseudomonas alcligenes* | − |
| *Enterococcus agglomerans* | − |
| *Haemophilis parainfluenzae* | − |
| *Haemophilis influenzae* | − |
| *Haemophilis haemolyticus* | − |
| *Haemophilis parahaemolyticus* | − |
| fungi | |
| *Candida albicans* (40083) | + |
| *Candida albicans* (40084) | + |

TABLE 1-continued

| Strain Name | Reactivity |
| --- | --- |
| Candida albicans (40107) | ++ |
| Candida albicans (7N) | ++ |
| Candida albicans (1623) | + |
| Candida albicans (clinical isolate) | ++ |
| Candida krusei | ++ |
| Candida tropicalis | ++ |
| Candida parapsilosis | ++ |
| Candida guilliermondii | + |
| Aspergillus fumigatus (0063) | − |
| Aspergillus flavus | − |
| Cryptococcus neoformans (0354) | − |
| Mucor spinosus (1322) | − |

Note: Denotation of "++" refers to the presence of a remarkable signal on hybridization, denotation of "+" refers to the presence of a signal on hybridization, while that of "−" refers to the absence of a signal on hybridization.

Apparently from Table 1 above, the probe of the present invention has reacted specifically with only the DNA obtained from several fungi and not cross-reacted with any DNA obtained from bacteria, therefore, its specificity to fungi has been confirmed.

EXAMPLE 2

Analysis of Base Sequence

A base sequence of DNA probe which has been confirmed its specificity to the fungi in the Example 1, was sequenced according to the following method.

(1) Preparation of Plasmid DNA

*Escherichia coli* K-12, JM109 transformant, wherein the subcloned insert fragments (to be sequenced) are contained in pGem-3Z (Promega), was inoculated in 5 ml of Luda-Bactani Medium (bacto-tryptone, 10 g/1 L; bacto-yeast extract, 5 g/1 L; NaCl, 10 g/1 L; adjusted pH to 7.0 with 5N NaOH) and cultured overnight.

Culture liquid was centrifuged (5,000 rpm, 5 min.) to collect the fungi. One hundred µl of a solution of 50 mM glucose/50 mM Tris-HCl (pH 8.0)/10 mM EDTA containing 2.5 mg/ml of lysozyme (Sigma) was added to the precipitate, and left at room temperature for 5 minutes. 0.2M NaOH solution containing 1% of sodium dodecyl sulfate (Sigma) was added to the suspension so obtained and mixed therewith. One hundred and fifty µl of 5M potassium acetate solution (pH 4.8) was further added thereto and mixed therewith, then iced for 15 minutes.

The supernatant obtained by centrifugation (15,000 rpm, 15 min.) was treated with phenol/CHCl$_3$ and added thereto ethanol of two times by volume, then the precipitate was obtained by centrifugation (12,000 rpm, 5 min.). This precipitate was dissolved in 100 µl of solution of 10 mM Tris-HCl (pH 7.5)/0.1 mM EDTA and added thereto 10 mg/ml RNaseA (Sigma) solution, then left it at room temperature for 15 minutes.

Three hundred µl of 0.1M sodium acetate solution (pH 4.8) was added to this preparation and treated with phenol/CHCl$_3$, then the precipitate was obtained therefrom by adding ethanol to the supernatant. This precipitate was dried and dissolved in 10 µl of distilled water to give DNA samples.

(2) Pretreatment for Sequencing

Pretreatment for sequencing was performed with Auto-Read™ Sequencing Kit (Pharmacia).

Concentration of DNA to become a template was adjusted to 5–10 µg in 32 µl of solution. Thirty two µl of the template DNA was transferred to 1.5 ml mini-tube (Eppendolf), and added thereto 8 µl of 2M NaOH solution, then mixed gently therewith. After instant centrifugation, it was left at room temperature for 10 minutes.

Seven µl of 3M sodium acetate (pH 4.8) and 4 µl of distilled water, then 120 µl of ethanol were added thereto then mixed therewith, and left it for 15 minutes on dry ice. DNA which has been precipitated by centrifugation for 15 minutes were collected, and the supernatant was removed carefully. The precipitate so obtained was washed with 70% ethanol and centrifuged for 10 minutes. Then, after the supernatant was removed carefully again, the precipitate was dried under the reduced pressure.

The precipitate was dissolved in 10 µl of distilled water, then 2 µl of fluorescent primer (0.42 A$_{260}$ unit/10 ml, 4–6 pmol [Fluorescent Primer; M13 Universal Primer: 5'-Fluorescein-d[CGACGTTGTAAAACGACGGCCAGT] -3' (SEQ ID No:7) (1.6 pmol/µl, 0.42 A$_{260}$ unit/ml); M13 Reverse Primer: 5'-Fluorescein-d [CAGGAAACAGCTATGAC]-3' (SEQ ID No.8) (2.1 pmol/ µl, 0.42 A$_{260}$ unit/ml)] and 2 µl of buffer for annealing was added thereto, and mixed gently.

After instant centrifugation, the mixture was heat-treated at 65° C. for 5 minutes and rapidly transferred to a circumstance of 37° C. and kept the temperature for 10 minutes there. After keeping the temperature, it was left at room temperature for 10 minutes or more and centrifuged instantly. Then, the sample was prepared by adding thereto 1 µl of a buffer for elongation and 3 µl of dimethyl sulfoxide.

Four mini-tubes have been identified with one of marks of "A", "C", "G" and "T", and, according to the mark, 2.5 µl of A Mix (dissolved ddATP with dATP, dCTP, c$^7$dGTP and dTTP), C Mix (dissolved ddCTP with dATP, dCTP, c$^7$dGTP and dTTP), G Mix (dissolved ddGTP with dATP, dCTP, c$^7$dGTP and dTTP), and T Mix (dissolved ddTTP with dATP, dCTP, c$^7$dGTP and dTTP) were poured into each identified tube. Each solution was preserved on ice before use, and was kept at 37° C. for one minute or more when used.

Two µl of diluted T7DNA polymerase (Pharmacia; 6–8 units/2 µl) was added to the DNA sample, and completely mixed by pipetting or mixing it gently. Immediately after completing the mixing, the mixed solution was distributed to 4.5 µl of the four types of solution respectively which have been kept at the temperature. Fresh tips were used at the each time of distribution.

The solution has been kept for 5 minutes at 37° C., then 5 µl of termination solution was added to each reaction-solution.

Fresh tips were also used for this step. Immediately after keeping the solution for 2–3 minutes at 90° C., it was cooled on ice. 4–6 µl/lane of the solution was applied to the electrophoresis.

(3) Sequencing on Base Sequence

Sequencing on base sequence of the probe disclosed in Example 1, having the specificity against *Candida albicans* was performed using A.L.F. DNA Sequencer System (Pharmacia) under an electrophoresis condition of 45° C. for 6 hours. As a result thereof, the total base sequence of *Candida albicans* CA-26 (SEQ ID No.1) has been clarified.

Moreover, details of the total base sequence were analyzed and three sites of the sequence (SEQ ID Nos.2, 3 and 4) contained in said total sequence were selected which shall become the basis of the probes (Template DNA) in the following Example 3.

EXAMPLE 3

Amplification of Template DNA by PCR Technique (1) Preparation of the reagent

The following reagent was prepared by mixing according to the order of (a) to (e).

(a) 10-fold diluted buffer: 2 µl
(b) 0.5 nM of dATP, dCTP, dGTP and dTTP: 1 µl, respectively (c) oligonucleotide primer No. 14 (20 mer: SEQ ID No.5): 2 µl oligonucleotide primer No. 17 (20 mer: SEQ ID No.6): 2 µl (d) Template DNA: 5 ng/2 µl (e) Taq polymerase (Cetus): 1.25 U/0.25 µl (2) Amplification of Template DNA Amplification of template DNA was performed using the prepared reagent and DNA amplifier (Trade Name: "BiGene PHC-1", Techne).

Thermal control of said DNA amplifier was set as follows and the reaction cycle was repeated 30 times: 94° C., for 1 minute for heat denaturation; 62° C., for 1 minute for annealing of the primer; and 74° C. for 1 minute for synthesis of complementary chain.

(3) Evaluation on Specificity of Template DNA and DNA from Bacteria by Hybridization Technique (a) Ten µl of the product obtained from amplification of template DNA having a base sequence of SEQ ID No. 2 were placed on a 2% agarose gel (Seakern GTG Agarose). After the gel was stained with ethidium bromide, alkaline denaturation by washing with 0.5N NaOH-1.5M NaCl for 30 minutes and neutralizing with 0.5M Tris-Cl (pH 7.5)-1.5M NaCl for 10 minutes were performed, then the gel was moved on a Byodyne nylon filter (type B) and stood for 12 hours to give the air-dried filter as a sample for Southern hybridization. Hybridization to genomic DNA from each of the fungi and bacteria shown in the following table 2 (each number of strain is corresponding to the number of lane in FIGS. 2 and 3) was then performed overnight under the condition of 45% formamide, 5×SSC at 42° C. after prehybridization under the same condition at 42° C. for two hours. For 3'-terminal of the probe, labelled oligonucleotide of 20 mer by means of DIG Oligonucleotide 3'-Endo Labeling Kit (Cat. No. 1362372: Boehringer Mannheim Biochimica) was employed.

TABLE 2

| No. | Strain Name of Fungi |
|---|---|
| 1 | Candida albicans (40083) |
| 2 | Candida albicans (40084) |
| 3 | Candida albicans (40107) |
| 4 | Candida albicans (7N) |
| 5 | Candida albicans (1623) |
| 6 | Candida albicans (clinical isolate) |
| 7 | Candida guilliermondii |
| 8 | Candida krusei |
| 9 | Candida parapsilosis |
| 10 | Candida tropicalis |
| 11 | Cryptococcus neoformans (0354) |
| 12 | Aspergillus flavus (0057) |
| 13 | Aspergillus fumigatus (0063) |
| 14 | Mucor spinosus (1322) |
| 15 | Absidia corymbifera (2435) |
|   | Strain Name of Bacteria |
| 16 | Staphylococcus aureus (ATCC 25923) |
| 17 | Staphylococcus epidermidis |
| 18 | Escherichia coli (ATCC 25922) |
| 19 | Klebsiella pneumoniae |
| 20 | Pseudomonas aeruginosa (ATCC 27853) |
| 21 | Haemophilis influenzae |

Note: As a molecular marker, pBR328 (BgII-HincII: Boehringer Mannheim) was employed on both edge lanes.

The sample which has been completed the overnight hybridization was washed with 1×SSC, 0.1% SDS for 10 minutes at 50° C. and with 0.5×SSC, 0.1% SDS for 10 minutes at 50° C., then air-dried and kept under the condition of −40° C.

Figure 2:
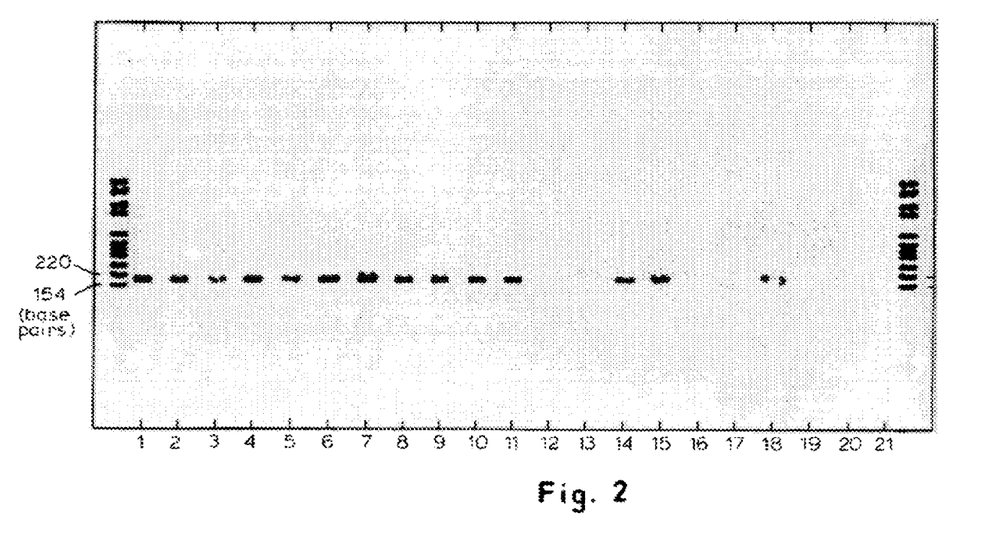
FIG. 2 is a result of electrophoresis showing the reactivities of a probe containing the base sequence of sequence identification number 2 against the genomic DNA from each kind of the fungi and the bacteria.

Apparently from the result of electrophoresis shown in FIG. 2, reactivities of the probe prepared from template DNA having a base sequence of SEQ ID No:2 against genomic DNA preserved by the fungi have been confirmed.

Figure 3:
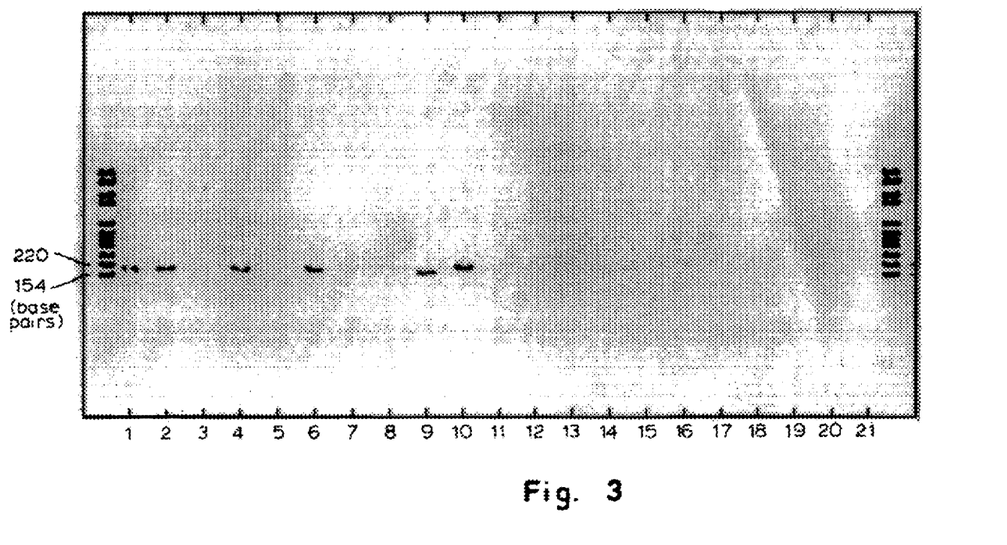
FIG. 3 is a result of electrophoresis showing the reactivities of a probe containing the base sequence of sequence identification number 3 against the genomic DNA from each kind of the fungi and the bacteria.

(b) Southern hybridization was similarly performed in accordance with the method described in the above (a), employing ten µl of the product obtained by amplification of template DNA having a base sequence of SEQ ID No:3. The results thereof are shown in FIG. 3.

Consequently, the reactivities of the probe prepared from template DNA having a base sequence of SEQ ID No:3 against the bacteria have not been confirmed, but only to the genomic DNA from the fungi.

(c) Then, a sample for Southern hybridization was prepared in accordance with the method described in the above (a) from 10 µl of the product obtained by amplification of template DNA having a base sequence of SEQ ID No: 4, and hybridization to genomic DNA from each of the fungi and bacteria shown in the following table 3 (each number is corresponding to the number of lane in FIG. 4) was performed.

TABLE 3

| No. | Strain Name of Fungi |
|---|---|
| 1 | Candida albicans (40083) |
| 2 | Candida albicans (40084) |
| 3 | Candida albicans (40009) |
| 4 | Candida guilliermondii (clinical isolate) |
| 5 | Candida krusei (clinical isolate) |
| 6 | Candida parasilosis (clinical isolate) |
| 7 | Candida tropicalis (clinical isolate) |
| 8 | Cryptococcus neoformans (0354) |
| 9 | Aspergillus flavus (0057) |
| 10 | Aspergillus fumigatus (0063) |
| 11 | Mucor spinosus (1322) |
| 12 | Absidia corymbifera (2435) |
|   | Strain Name of Bacteria |
| 13 | Staphylococcus aureus (ATCC 25923) |
| 14 | Staphylococcus epidermidis (ATCC 12228) |
| 15 | Escherichia coli (ATCC 25922) |
| 16 | Klebsiella pneumoniae (clinical isolate) |
| 17 | Pseudomonas aeruginosa (ATCC 27853) |
| 18 | Enterobacter agglomerans (clinical isolate) |
| 19 | Streptococcus pneumoniae (HYSDH DP-2) |
| 20 | Streptococcus faecalis (ATCC 29212) |
| 21 | human genomic DNA |

Note: As a molecular marker, φ X174/HaeIII was employed on both edge lanes.

Figure 4:
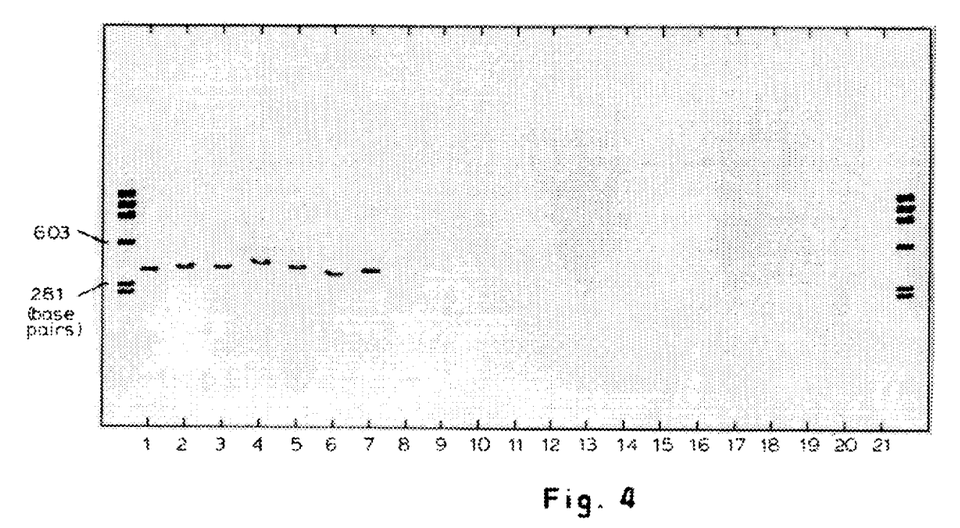
FIG. 4 is a result of electrophoresis showing the reactivities of a probe containing the base sequence of sequence identification number 4 against the genomic DNA from each kind of the fungi and the bacteria.

As a result thereof, specific reactivities of the probe prepared from template DNA having a base sequence of SEQ ID No:4 to genomic DNA from the fungi belonging to genus Candida have been confirmed (FIG. 4).

(d) Finally, sensitivity for detection of the probe of the present invention and cross reactivities against human genomic DNA were evaluated.

Namely, a sample for Southern hybridization was prepared in accordance with the method described in the above (a) from 10 µl of the product obtained by amplification of template DNA having a base sequence of SEQ ID No:2, and hybridization to genomic DNA from Candida albicans adjusted to various concentrations and to each human genomic DNA from four healthy adult male shown in the following table 4 (each number is corresponding to the number of lane in FIG. 5) was performed.

TABLE 4

| No. | |
|---|---|
| | Strain Name of Fungi |
| 1 | Candida albicans (50 ng) |
| 2 | Candida albicans (25 ng) |
| 3 | Candida albicans (10 ng) |
| 4 | Candida albicans (5 ng) |
| 5 | Candida albicans (1 ng) |
| 6 | Candida albicans (0.5 ng) |
| 7 | Candida albicans (0.1 ng) |
| 8 | Candida albicans (0.05 ng) |
| 9 | Candida albicans (0.01 ng) |
| 10 | Candida albicans (5 pg) |
| 11 | Candida albicans (1 pg) |
| | Strain Name of Bacteria |
| 12 | Candida albicans (40083) |
| 13 | human genomic DNA 1 |
| 14 | human genomic DNA 2 |
| 15 | human genomic DNA 3 |
| 16 | human genomic DNA 4 |

Note: As a molecular marker, pBR328[BgIII-HincII] was employed on both edge lanes.

Figure 5:
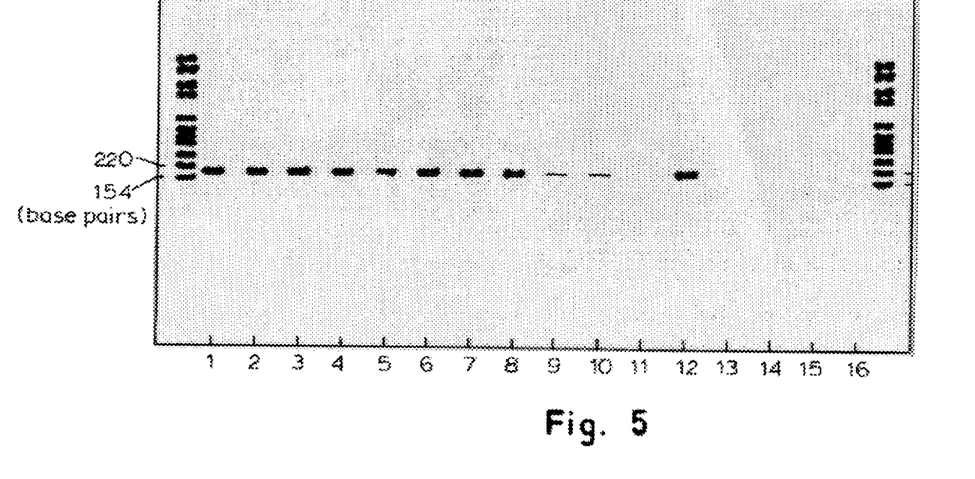
FIG. 5 is a result of electrophoresis showing the reactivities of a probe containing the base sequence of sequence identification number 2 against various concentrations of the genomic DNA derived from *Candida albicans* and human.

Apparently from the results shown in FIG. 5, it was proved that the probe of the present invention could detect genomic DNA from Candida albicans at such a low concentration as 5 pg/µl and have not cross-reacted to human genomic DNA.

Industrial Applicability

According to a probe of the present invention, fungi can be directly detected without proliferating the fungi, and rapidly and exactly identified. That is to say, according to the diagnosis using the probe of the present invention, identification of the fungi can be realized with single specimen, then, the necessary time for diagnosis can be reduced to about one to two days, while the conventional method (with low detection rate) required 3-4 days, and the detection rate is remarkably improved. Therefore, the present invention can provide an objective factors for the treatment of fungemia, then realize the effective treatment in the early stage of the infectious diseases, as well as expectations to reduction of the mortality.

Then, by clarifying the base sequences of the probes which specifically react with Candida albicans, one of the most frequently observed causative fungi of fungemia, artificial preparation of these probes can also be realized.

Further, by comparing base sequences of genomic DNA from the clinical specimen with that of the present invention, rapid identification of the species of the causative fungi of infectious diseases can be realized.

As stated above, the present invention provides a desired probe for diagnosing the infectious diseases, besides, excellent utilities as a guide for preparing a PCR primer and as a standard sequence suitable for the comparison and reference of genomic DNA from the clinical specimen are expected, and further outstanding effects, for example, of providing valuable clues for preparation and development of the other probes which specifically react with causative fungi of the fungemia.

Moreover, since the base sequence disclosed in the present application was obtained by random-cloning of the genomic DNA from clinical isolates, utilities of the base sequence of the present invention should be extended to the complementary strand thereof.

Further, although it may be thought that DNA obtained from the wild strains might contain the mutated portion, apparently from the disclosure of the Examples above, said mutated DNA portion would not affect the utilities to be derived by the present invention comprising the specificity of the probe of the present invention in the hybridization for a diagnosis of the infectious diseases, and usage of the information on the base sequence disclosed in the present application to design the primer for PCR technique with the aim of a rapid diagnosis of the infectious diseases.

---

We claim:

1. A purified and isolated *C. albicans* nucleic acid fragment useful for diagnosing infectious diseases, said nucleic acid comprising a nucleotide sequence selected from the group consisting of SEQ ID NO: 1, SEQ ID NO: 3, and SEQ ID NO: 4.

2. A purified and isolated nucleic acid fragment according to claim 1, said nucleic acid fragment comprising a nucleotide sequence set forth in SEQ ID NO: 1.

3. A purified and isolated nucleic acid fragment according to claim 2, wherein the nucleotide sequence of said nucleic acid fragment is the sequence set forth in SEQ ID NO: 1.

4. A purified and isolated nucleic acid fragment according to claim 1, said nucleic acid fragment comprising a nucleotide sequence set forth in SEQ ID NO: 3.

5. A purified and isolated nucleic acid fragment according to claim 4, wherein the nucleotide sequence of said nucleic acid fragment is the sequence set forth in SEQ ID NO: 3.

6. A purified and isolated nucleic acid fragment according to claim 1, said nucleic acid fragment comprising a nucleotide sequence set forth in SEQ ID NO: 4.

7. A purified and isolated nucleic acid fragment according to claim 6, wherein the nucleotide sequence of said nucleic acid fragment is the sequence set forth in SEQ ID NO: 4.

8. A *C. albicans* nucleic acid fragment according to any one of claims 1–7 wherein the nucleic acid further comprises a detectable label.

9. A purified and isolated polynucleotide probe for diagnosing infectious diseases, said probe comprising a nucleotide sequence selected from the group consisting of SEQ ID NO: 3 and SEQ ID NO: 4, said probe being capable of hybridizing with DNA from *Candida albicans* and failing to hybridize to human genomic DNA under the following hybridization conditions:

(a) prehybridization/hybridization buffer comprising 45% formamide and 5×SSC;

(b) prehybridization at 42° C. for two hours;

(c) hybridization overnight at 42° C.;

(d) washing for 10 minutes at 50° C. using a wash solution comprising 1×SSC and 0.1% SDS;

(e) washing for 10 minutes at 50° C. using a wash solution comprising 0.5×SSC and 0.1% SDS.

10. A polynucleotide probe according to claim 9 comprising the nucleotide sequence set forth in SEQ ID NO: 4.

11. A polynucleotide probe according to claim 9 wherein said probe hybridizes to genomic DNA from a plurality of fungi of the genus Candida and wherein said probe fails to hybridize to genomic DNA from a fungus selected from the group consisting of *Cryptococcus neoformans*, *Aspergillus flavus*, *Aspergillus fumigatus*, *Mucor spinosus*, and *Absidia corymbifera*.

12. A polynucleotide probe according to any one of claims 9–11 wherein said probe further comprises a detectable label.

13. A purified and isolated nucleic acid useful for diagnosing infectious diseases, said nucleic acid consisting of a nucleotide sequence derived from *C. albicans* and at least one heterologous nucleotide sequence, said nucleotide sequence derived from *C. albicans* consisting of one of SEQ ID NO: 1, SEQ ID NO: 3, and SEQ ID NO: 4.

* * * * *

UNITED STATES PATENT AND TRADEMARK OFFICE
CERTIFICATE OF CORRECTION

PATENT NO. : 5,708,159
DATED : January 13, 1998
INVENTOR(S) : Ohno et al.

It is certified that error appears in the above-identified patent and that said Letters Patent is hereby corrected as shown below:

Column 1, line 16, delete "in vivo" and insert --*in vivo*--.

Column 5, line 33, delete "Luda-" and insert --Luria---.

Column 6, line 34, delete "Two$\mu$l" and insert --Two $\mu$l--.

Signed and Sealed this

Eighteenth Day of May, 1999

*Attest:*

*Attesting Officer*

Q. TODD DICKINSON

Acting Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 899 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Candida albicans
        ( B ) STRAIN: Clinical Isolate CA- 26

( x i ) SEQUENCE DESCRIPTION: SEQ ID NO:1:

```
GAATTCCTAG TAAGCGCAAG TCATCAGCTT GCGTTGATTA CGTCCCTGCC CTTTGTACAC        60

ACCGCCCGTC GCTACTACCG ATTGAATGGC TTAGTGAGGC CTCCGGATTG GTTTAGGAAA       120

GGGGGCAACC TCATTCTGGA ACCGAGAAGC TGGTCAAACT TGGTCATTTA GAGGAAGTAA       180

AAGTCGTAAC AAGGTTTCCG TAGTGAACCT GCGGAAGGAT CATTACTGAT TTGCTTAATT       240
```

```
GCACCACATG TGTTTTTCTT TGAACAAACT TGCTTTGCGG TGGGCCCAGC CTGCCGCCAG    300

AGGTCTAAAC TTACAACCAA TTTTTTATCA ACTTGTCACA CCAGATTATT ACTTAATAGT    360

CAAACTTCAA CAAACGGATC TCTTGGTTCT CGCAGCGAAA TGCGATACGT AATATGAATT    420

GCAGATATTC GTGAATCATC GAATCTTTGA ACGCACATTG CGCCCTCTGG TATTCCGGAG    480

GGCATGCCTG TTTGAGCGTC GTTTCTCCCT CAAACCGCTG GGTTTGGTGT TGAGCAATAC    540

GACTTGGGTT TGCTTGAAAG ACGGTAGTGG TAAGGCGGGA TCGTTTGACA ATGGCTTAGG    600

TCTAACCAAA AACATTGCTT GCGGCGGTAA CGTCCACCAC GTATATCTTC AAACTTTGAC    660

CTCAAATCAG GTAGGACTAC CCGCTGAACT TAAGCATATC AATAAGCGGA GGAAAAGAAA    720

CCAACAGGGA TTGCCTCAGT AGCGGCGAGT GAAGCGGCAA AAGCTCAAAT TTGAAATCTG    780

GCGTCTTTGG CGTCCGAGTT GTAATTTGAA GAAGGTATCT TTGGGCCCGG CTCTTGTCTA    840

TGTTCCTTGG AACAGGACGT CACAGAGGGT GAGAATCCCG TGCGATGAGA TGACCCGGG    899
```

( 2 ) INFORMATION FOR SEQ ID NO:2:

( i ) SEQUENCE CHARACTERISTICS:
        ( A ) LENGTH: 189 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Candida albicans
        ( B ) STRAIN: Clinical Isolate CA- 26

( x i ) SEQUENCE DESCRIPTION: SEQ ID NO:2:

```
GCGCAAGTCA TCAGCTTGCG TTGATTACGT CCCTGCCCTT TGTACACACC GCCCGTCGCT     60

ACTACCGATT GAATGGCTTA GTGAGGCCTC CGGATTGGTT TAGGAAAGGG GGCAACCTCA    120

TTCTGGAACC GAGAAGCTGG TCAAACTTGG TCATTTAGAG GAAGTAAAAG TCGTAACAAG    180

GTTTCCGTA                                                            189
```

( 2 ) INFORMATION FOR SEQ ID NO:3:

( i ) SEQUENCE CHARACTERISTICS:
        ( A ) LENGTH: 224 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Candida albicans
        ( B ) STRAIN: Clinical Isolate CA- 26

( x i ) SEQUENCE DESCRIPTION: SEQ ID NO:3:

```
GCTGGGTTTG GTGTTGAGCA ATACGACTTG GGTTTGCTTG AAAGACGGTA GTGGTAAGGC     60

GGATCGTTT GACAATGGCT TAGGTCTAAC CAAAAACATT GCTTGCGGCG GTAACGTCCA    120

CCACGTATAT CTTCAAACTT TGACCTCAAA TCAGGTAGGA CTACCCGCTG AACTTAAGCA    180

TATCAATAAG CGGAGGAAAA GAAACCAACA GGGATTGCCT CAGT                    224
```

( 2 ) INFORMATION FOR SEQ ID NO:4:

( i ) SEQUENCE CHARACTERISTICS:
        ( A ) LENGTH: 369 base pairs
        ( B ) TYPE: nucleic acid
        ( C ) STRANDEDNESS: double (D) TOPOLOGY: linear (ii) MOLECULE TYPE: DNA (genomic)

(vi) ORIGINAL SOURCE:
    (A) ORGANISM: Candida albicans
    (B) STRAIN: Clinical Isolate CA-26

(xi) SEQUENCE DESCRIPTION: SEQ ID NO:4:

| | | | | | | |
|---|---|---|---|---|---|---|
| AAACGGATCT | CTTGGTTCTC | GCAGCGAAAT | GCGATACGTA | ATATGAATTG | CAGATATTCG | 60 |
| TGAATCATCG | AATCTTTGAA | CGCACATTGC | GCCCTCTGGT | ATTCCGGAGG | GCATGCCTGT | 120 |
| TTGAGCGTCG | TTTCTCCCTC | AAACCGCTGG | GTTGGTGTT | GAGCAATACG | ACTTGGGTTT | 180 |
| GCTTGAAAGA | CGGTAGTGGT | AAGGCGGGAT | CGTTTGACAA | TGGCTTAGGT | CTAACCAAAA | 240 |
| ACATTGCTTG | CGGCGGTAAC | GTCCACCACG | TATATCTTCA | AACTTTGACC | TCAAATCAGG | 300 |
| TAGGACTACC | CGCTGAACTT | AAGCATATCA | ATAAGCGGAG | GAAAAGAAAC | CAACAGGGAT | 360 |
| TGCCTCAGT | | | | | | 369 |

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc ="Synthetic DNA"

(iv) ANTI-SENSE: NO

(xi) SEQUENCE DESCRIPTION: SEQ ID NO:5:

GACAATGGCT TAGGTCTAAC                                                                               20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc ="Synthetic DNA"

(iv) ANTI-SENSE: NO

(xi) SEQUENCE DESCRIPTION: SEQ ID NO:6:

TCATCTCATC GCACGGGATT                                                                              20

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc ="Synthetic DNA"

(iv) ANTI-SENSE: NO

(xi) SEQUENCE DESCRIPTION: SEQ ID NO:7:

CGACGTTGTA AAACGACGGC CAGT                                                        24

(2) INFORMATION FOR SEQ ID NO:8:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc ="Synthetic DNA"

(iv) ANTI-SENSE: NO (xi) SEQUENCE DESCRIPTION: SEQ ID NO:8:

CAGGAAACAG CTATGAC    17